United States Patent [19]

Weers

[11] Patent Number: 4,871,374

[45] Date of Patent: Oct. 3, 1989

[54] FUEL OILS STABILIZED WITH IMINE-ENAMINE CONDENSATES AND METHOD THEREOF

[75] Inventor: Jerry J. Weers, Ballwin, Mo.

[73] Assignee: Petrolite Corporation, St. Louis, Mo.

[21] Appl. No.: 143,894

[22] Filed: Jan. 14, 1988

[51] Int. Cl.$^4$ ............................................. C10L 1/22
[52] U.S. Cl. ............................................. 44/63; 44/73
[58] Field of Search ...................................... 44/63, 73

[56] References Cited

U.S. PATENT DOCUMENTS

| | | | |
|---|---|---|---|
| 2,055,810 | 9/1936 | Bartram | 44/73 |
| 2,264,894 | 12/1941 | Shoemaker et al. | 44/73 |
| 2,265,051 | 12/1941 | Adams | 44/9 |
| 3,364,000 | 1/1968 | Stromberg | 44/69 |
| 3,486,866 | 12/1969 | Stromberg et al. | 44/72 |
| 3,510,282 | 5/1970 | Seffens | 44/63 |
| 3,640,692 | 2/1972 | Rakow et al. | 44/73 |
| 3,654,346 | 4/1972 | Godar et al. | 260/482 R |
| 3,821,302 | 6/1974 | Hu | 44/73 |
| 3,859,211 | 1/1975 | Redmore | 210/54 |
| 4,163,646 | 8/1979 | Oude Alink et al. | 44/73 |
| 4,537,601 | 8/1985 | Naiman | 44/62 |

Primary Examiner—William R. Dixon, Jr.
Assistant Examiner—Jerry D. Johnson
Attorney, Agent, or Firm—Grace J. Fishel; Stanley M. Tarter

[57] ABSTRACT

A fuel oil stabilized with an imine-enamine condensate which is the reaction product of an aldehyde having at least two carbon atoms and/or a ketone and a polyamine of the formula:

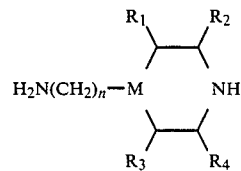

wherein n is 0 or an integer from 1 to 6, M is a carbon or nitrogen atom and $R_1$, $R_2$, $R_3$ and $R_4$ are independently hydrogen, a saturated or unsaturated hydrocarbon group, e.g., alkyl, aryl, aralky, alkaryl, cycloalkyl, alkenyl, aralkenyl, alkenylaryl, cycloalkenyl and the like or heterocyclyl groups. A method of stabilizing a fuel oil wherein a stabilizing amount of the above mentioned imine-enamine condensate is incorporated into the fuel oil.

12 Claims, No Drawings

FUEL OILS STABILIZED WITH IMINE-ENAMINE CONDENSATES AND METHOD THEREOF

BACKGROUND OF THE INVENTION

1. Field of the Invention

This invention relates to stabilization of fuel oils with an imine-enamine condensate.

More particularly, the present invention relates to stabilization of fuel oils, particularly those from naphthenic crudes, with an imine-enamine condensate comprising the reaction product of an aldehyde having at least two carbon atoms and/or a ketone and a polyamino compound of the formula:

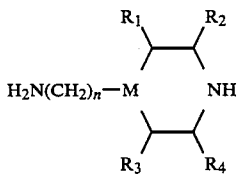

wherein n is 0 or an integer from 1 to 6, M is a carbon or nitrogen atom and $R_1$, $R_2$, $R_3$ and $R_4$ are independently hydrogen, a saturated or unsaturated hydrocarbon group, e.g., alkyl, aryl, aralkyl, alkaryl, cycloalkyl, alkenyl, aralkenyl, alkenylaryl, cycloalkenyl and the like or heterocyclyl groups.

Accordingly, it is an object of the present invention to provide a fuel oil which is stabilized with an imine-enamine condensate as herein described.

A further object of the invention is to provide a method for stabilizing a fuel oil with said imine-enamine condensate.

Other objects and features of the invention will be in part apparent and in part pointed out hereinafter, the scope of the invention being indicated by the subjoined claims.

2. Prior Art

The condensation products of a number of linear polyamines containing a primary and a secondary amino group with aldehydes and ketones are known to be useful as fuel stabilizers. In these products, however, if the secondary amine reacts at all, it is to form a heterocyclyl ring with a methylene or substituted methylene group between the nitrogen atom of the secondary amino group and the nitrogen atom of the second amino group with which it is linked.

SUMMARY OF THE INVENTION

The present invention is concerned with an additive which is the condensation product of an aldehyde having at least two carbon atoms and/or a ketone and a polyamino compound of the formula:

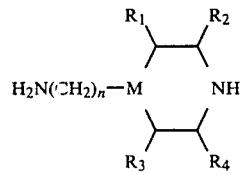

wherein n is 0 or an integer from 1 to 6, M is a carbon or nitrogen atom and $R_1$, $R_2$, $R_3$ and $R_4$ are independently hydrogen, a saturated or unsaturated hydrocarbon group, e.g., alkyl, aryl, aralkyl, alkaryl, cycloalkyl, alkenyl, aralkenyl, alkenylaryl, cycloalkenyl and the like or heterocyclyl groups.

The chemical composition of a fuel oil effects its stability and its demands for stabilization, such that different additives are useful in different fuel oils. Condensation products in accordance with the present invention are particularly effective at stabilizing fuel oils with a high acid number, e.g., fuel oils from naphthenic crudes.

DETAILED DESCRIPTION OF THE INVENTION

It has now been discovered that fuel oils can be stabilized with an imine-enamine condensate which is the reaction product of a polyamino compound of the formula:

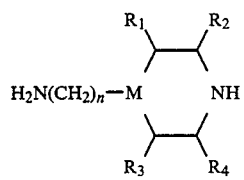

wherein n is 0 or an integer from 1 to 6, M is CH or nitrogen and $R_1$, $R_2$, $R_3$ and $R_4$ are independently hydrogen, a saturated or unsaturated hydrocarbon group, e.g., alkyl, aryl, aralkyl, alkaryl, cycloalkyl, alkenyl, aralkenyl, alkenylaryl, cycloalkenyl and the like or heterocyclyl groups with an aldehyde having at least two carbon atoms and/or a ketone.

More specifically, the imine-enamine condensates which are the subject of the present invention are obtained by reacting a polyamino compound of the above formula in which the alkyl or alkenyl portion of the alkyl, aralkyl, alkaryl, alkenyl, aralkenyl or alkenylaryl groups for $R_1$–$R_4$ contains about 1 to 6 carbon atoms, straight or branched chain, so long as the condensation product is soluble in middle distillate fuels and preferably insoluble or only slightly soluble in water such that it is not extracted from the fuel. $R_1$–$R_4$ may also be substituted with groups which do not compete with the condensation reaction. When $R_3$ or $R_4$ are other than hydrogen, for example, t-butyl, steric hindrance about the secondary amino group favors the condensation reaction and formation of the enamine group. Examples of polyamino compounds include 1-piperazineamine, 1-piperaz inemethanamine, 1-piperazineethanamine, 1-piperazinepropanamine, 4-aminopiperidine, 4-(aminomethyl)piperidine, 4-(2-aminoethyl)-piperidine, 4-(3-aminopropyl)piperidine and the like.

Aldehydes having at least two carbon atoms and/or ketones useful in the present invention have the general formula:

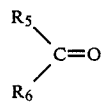

in which $R_5$ may be a saturated or unsaturated hydrocarbon group, e.g., alkyl, aryl, aralkyl, alkaryl, cycloalkyl, alkenyl, aralkenyl, alkenylaryl, cycloalkenyl and the like or heterocyclyl groups and $R_6$ may be a hydrogen, a saturated or unsaturated hydrocarbon group, e.g., alkyl, aryl, aralkyl, alkaryl, cycloalkyl, alkenyl, aralkenyl, alkenylaryl, cycloalkenyl and the like or heterocyclyl groups as described for $R_1$-$R_4$. Examples of aldehydes or ketones which may be employed in the condensation reaction include dimethyl ketone, methyl ethyl ketone, methyl isobutyl ketone, cyclohexanone, n-butyraldehyde, isobutyraldehyde, 2-ethyl butyraldehyde, benzaldehyde, acetophenone and the like.

The imine-enamine condensates useful in the subject invention may be prepared under conventional dehydrating conditions whereby water is removed by any suitable means. Depending on the reaction conditions, various side products may be formed but they usually do not effect the utility of the imine-enamine condensates so long as they are present in relatively minor amounts. Typically the aldehyde or ketone is added to a solution of the polyamino compound and the condensate recovered by distilling off the water and the solvent. Mixtures of different aldehydes, mixtures of different ketones, mixtures of aldehydes and ketones and mixtures of different polyamino compounds may also be used in the condensation reaction and mixtures of the reaction products thereof as described herein may be used as fuel stabilizers in accordance with the present invention. The reaction with ketones is slightly less favorable than with aldehydes and a catalyst such as toluene sulfonic acid, p-dodecylbenzene sulfonic acid or the like is preferably included to obtain a good yield. Suitable solvents include ether, benzene, alcohol, hexane and xylene, although other solvents may be used. Solvents with lower boiling points are preferred since the reaction product tends to decompose at higher temperatures.

Depending on the molar ratio of the aldehyde or ketone to the polyamino compound in the reaction mixture, the solvent and other such variables, the proportion of the aldehyde or ketone reacting with both the primary and secondary amino groups may be effected other than when $R_5$ is aryl and $R_6$ is hydrogen such that either the singly reacted imine or the doubly reacted imine-enamine condensation product is formed, both of which are useful in the present invention. When $R_5$ is aryl and $R_6$ is hydrogen, it will be understood that only the imine condensation product can be formed but the unreacted secondary amino group contributes to the activity of the reaction product as a fuel stabilizer as in other singly reacted condensation products as herein described. For lower molecular weight aldehydes and ketones other than benzaldehyde or the like, it is preferred that the molar ratio of the aldehyde or ketone to the polyamino compound be substantially stoichiometric for the formation of the imine-enamine condensation product, i.e., 2:1 as opposed to 1:1 for the imine, since the doubly reacted imine-enamine condensation product is less soluble in water than the singly reacted imine product. In general, however, the molar ratio may vary from about 1:1 to about 2:1 but a molar ratio of 2:1 is preferred. On the other hand, for benzaldehyde or the like when $R_5$ is aryl and $R_6$ is hydrogen, a molar ratio of about 1:1 is preferred for the reason described above.

The fuel oils which are improved in accordance with the present invention are hydrocarbon fractions having an initial boiling point of at least 100 degrees F. and an end point not higher than about 750 degrees F. at atmospheric or reduced pressure, and boiling substantially continuously throughout their distillation range. Such fuel oils are generally known as distillate fuel oils. It will be understood, however, that this term is not restricted to straight-run distillate fractions. Thus, as is well known to those skilled in the art, the distillate fuel oils can be straight-run distillate fuel oils, catalytically or thermally cracked (including hydrocracked) distillate fuel oils, or mixtures of straight-run distillates, naphthas and the like, with cracked distillate stocks. Moreover, such fuel oils can be treated in accordance with well known commercial methods, such as acid or caustic treatment, solvent refining, clay treatment and so forth.

The distillate fuels are characterized by their relatively low viscosities, low pour points, and the like. The principal property which characterizes the contemplated hydrocarbon fractions, however, is the distillation range. As mentioned herein, this range will lie between about 100 degrees F. and about 750 degrees F. at atmospheric or reduced pressure. Obviously, the distillation range of each individual fuel oil will cover a narrow range falling, nevertheless, within the above-specified limits. Likewise, each fuel oil will boil substantially continuously throughout its distillation range.

Especially contemplated herein are Nos. 1, 2, 3, 4 and 6 fuel oils used in domestic heating and as diesel fuel oils, particularly those having a high acid number either initially or resulting from fuel degradation occurring during storage, i.e. at least 0.1 mg KOH/g fuel as determined by A.S.T.M. Specification D664, made up chiefly or entirely of distillate or cracked stocks from naphthenic crudes. In the case of Nos. 1, 2 and 3 fuel oils, the imine-enamine condensates as described herein are added primarily to improve color stability of the fuel, whereas in Nos. 4 and 6 fuel oils, the condensates are added primarily as sweeteners or to retard sedimentation. The domestic heating oils generally conform to the specifications set forth in A.S.T.M. Specifications D396-86. Specifications for diesel fuels are defined in A.S.T.M. Specifications D975-81.

The amount of imine-enamine condensate as herein defined effective to stabilize fuel oils will vary, depending on various factors, for example the particular oil to be stabilized and the conditions for storage. The stability of an oil depends largely on the nature of the crude oil from which it is made and the type of processing involved during refining and therefore some oils will require more additive to stabilize than others. In practice, at least about 0.0001% (1ppm) additive based on the weight of the oil is used, such as from about 0.0001 to 0.1% (1–1000 ppm), for example from about 0.0002 to 0.05% (2–500 ppm), but preferably from about 0.0003 to 0.03% (3–300 ppm). Larger amounts, such as 1% or higher, can be employed but in general there is usually no commercial advantage in doing so.

In accordance with common practice, the imine-enamine condensates as herein defined may be used in combination with other stabilizers. For example with fuel oils from naphthenic crudes, it is usually necessary to utilize the subject imine-enamine condensates with other stabilizers which are effective as dispersants. Metal deactivators may also be included for some applications. In most instances, however, it is not necessary to add sweeteners as the subject imine-enamine condensates scavenge hydrogen sulfide and mercaptans in addition to serving as color stabilizers for the fuel oil. Suitable dispersants for use in combination with the imine-enamine condensates as herein described include Mannich condensates of alkylphenols, formaldehyde and polyamines, although other dispersants may also be used.

The following examples illustrate the invention.

EXAMPLE 1

An imine-enamine condensation product of cyclohexanone and 1-piperazineethanamine was prepared as follows: In a round bottom flask fitted with a Dean Stark trap, 0.2 mole 1-piperazineethanamine and 0.4 mole cyclohexanone were diluted with xylenes to 75% activity by weight. An acid catalyst, p-dodecylbenzene sulfonic acid (0.5 g) was added and the mixture was heated to and held at 80 degrees C. with stirring for 30 minutes. Any water which was formed during the condensation reaction and the solvent xylenes were distilled from the flask under vacuum (100 mm Hg). The mixture was then heated until a temperature of 125 degrees C. was reached and then cooled forming:

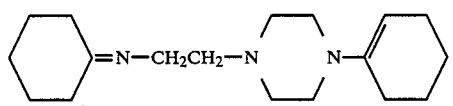

in good yield.

Throughout the following examples color stability was determined by A.S.T.M. Specification D-1500 and % T (light transmittance) was measured at 530 nm. The amount of solids was determined after storage under the indicated conditions by passing the exposed fuel through a moderately retentive Whatman 1 filter paper and noting the degree of stain on the filter paper. The filter paper pads were compared according to a rating of 1=best and 20=worst. In some instances, the amount of solids was determined by measuring the amount of filterable residue on the pad. The hydrogen sulfide or mercaptan content of the distillate fuel was determined by A.S.T.M. Specification 3227.

EXAMPLE 2

The 1:1 molar condensate of 1-piperazineethanamine and butyraldehyde (Additive I) was added to diesel fuel from a West Coast crude and tested for color stability as follows:

| Test Method: 10 day ambient storage of fuel | | |
|---|---|---|
| Additive | Conc(lb/mbbl) | D-1500 Color |
| Blank | — | 8.0 |
| Additive I | 100 | 6.0 |
| Additive II | 500 | <4.5 |

EXAMPLE 3

The 1:1 molar condensate of 1-piperazineethanamine and benzaldehyde (Additive II) was tested with Additive I as a color stabilizer in a fuel oil from a naphthenic crude having an initial acid number of 2.28 mg KOH/g fuel which rose to 2.35 mg KOH/g fuel in the untreated fuel by the end of the test as follows:

| Test Method: 90 min storage at 300 degrees F. | | | |
|---|---|---|---|
| Additive | Conc(lb/mbbl) | D-1500 Color | Residue Pad Rating |
| Blank | — | <6.5 | 1 |
| Additive I | 50 | 5.0 | 1 |
| | 75 | <4.5 | 1 |
| | 150 | 5.5 | 1 |
| Additive II | 50 | 5.0 | 1 |
| | 75 | <5.0 | 1 |
| | 150 | <5.5 | 1 |

EXAMPLE 4

The 2:1 molar condensate of 2-ethylbutyraldehyde and 1-piperazineethanamine (Additive III) and the 2:1 molar condensate of methyl ethyl ketone and 1-piperazineethanamine (Additive IV) were tested as a color stabilizer in light cycle oil having an initial acid number of 0.10 mg KOH/g fuel which rose to 0.15 mg KOH/g fuel in the untreated fuel at the end of the test as follows:

| Test Method: 90 min storage at 300 degrees F. | | | | |
|---|---|---|---|---|
| Additive | Conc(lb/mbbl) | D-1500 Color | % T | Residue Pad Rating |
| Blank | — | 8.0 | 0 | 12 |
| Additive II | 10 | 4.0 | 29 | 11 |
| | 15 | 3.5 | 36 | 10 |
| | 20 | 3.5 | 36 | 12 |
| | 25 | 3.5 | 33 | 10 |
| Additive IV | 10 | 4.0 | 26 | 8 |
| | 15 | 3.5 | 33 | 8 |
| | 20 | 3.5 | 34 | 9 |
| | 25 | 3.5 | 29 | 12 |

EXAMPLE 5

The 1:1 molar condensate of ethylbutyraldehyde and 1-piperazineethanamine (Additive V) and the 2:1 molar condensate thereof (Additive III) were tested as a color stabilizer in a fuel oil from a paraffinic crude to which 3000 pp thiophenol had been added and having an initial acid number of 0.04 mg KOH/g fuel which rose to 0.17 mg KOH/g fuel in the untreated fuel stored for 12 weeks at 110 degrees. An equal amount of an alkylphenol, formaldehyde and polyamine condensate was included as a dispersant. The results were as follows:

| Test Method: 4 weeks storage at 110 degrees F. | | |
|---|---|---|
| Additive | Conc(lb/mbbl) | D-1500 Color |
| Blank | — | 3.5 |
| Additive III + Dispersant | 100 | 2.5 |
| | 500 | 2.5 |
| | 1000 | 2.5 |
| Additive V + Dispersant | 100 | 3.0 |
| | 500 | 2.5 |
| | 1000 | 2.5 |

EXAMPLE 6

The 2:1 molar condensate of isobutyraldehyde and 1-piperazineethanamine (Additive VI), the 2:1 molar condensate of dimethyl ketone and 1-piperazineethanamine (Additive VII), the 2:1 molar condensate of cyclohexanone and 1-piperazineethanamine (Additive VIII) and Additives III, IV and V were tested as a color stabilizer in light cycle oil to which 3000 ppm thiophenol, 3000 ppm 1-dodecanethiol, 400 ppm quinoline, 400 ppm 2,5-dimethylpyrrole, 2000 ppm acetic acid and 1000 ppm cumene hydroperoxide had been added and having an initial acid number of 0.18 mg KOH/g fuel which rose to 0.22 mg KOH/g fuel in the untreated fuel —continued

| Test Method: 90 min storage at 300 degrees F. | | | |
|---|---|---|---|
| Additive | Conc(lb/mbbl) | D-1500 Color | Residue Pad Rating |
| | 150 | <5.5 | 1 | at the end of the test. In some instances the indicated amount of an alkylphenol, formaldehyde and polyamine condensate was included as a dispersant. The results were as follows:

| Test Method: 10 day storage at 110 degrees F. | | |
| --- | --- | --- |
| Additive | Conc(ppm) | D-1500 Color |
| Blank | — | 6.5 |
| Additive VI | 1000 | 5.0 |
| Additive VI + Dispersant | 333 + 666 | 2.5 |
| Additive III | 1000 | 5.5 |
| Additive III + Dispersant | 333 + 666 | 2.5 |
| Additive VII | 1000 | 5.5 |
| Additive VII + Dispersant | 333 + 666 | 2.5 |
| Additive VIII | 1000 | 3.5 |
| Additive VIII + Dispersant | 333 + 666 | 2.5 |
| Additive IV | 1000 | 4.5 |
| Additive IV + Dispersant | 333 + 666 | 2.5 |
| Additive V | 1000 | 5.0 |
| Additive V + Dispersant | 333 + 666 | 2.5 |

EXAMPLE 7

The 2:1 molar condensate of cyclohexanone and 1-piperazineethanamine (Additive VIII) was tested as a color stabilizier in diesel oil from a West Coast crude having an initial acid number of 0.6 mg KOH/g fuel which rose to 1.25 mg KOH/g fuel in the untreated fuel at the end of 12 weeks storage at 110 degrees F. with the indicated amount of an alkylphenol, formaldehyde and polyamine condensate included as a dispersant. The results under several test conditions were as follows:

| Test Method: 4 weeks storage at 110 degrees F. | | | |
| --- | --- | --- | --- |
| Additive | Conc(lb/mbbl) | D-1500 Color | % T |
| Blank | — | <3.5 | 20 |
| Additive VIII + Dispersant | 50 + 50 | 3.0 | 33 |
| Additive VIII + Dispersant | 100 + 100 | 3.0 | 37.5 |
| Additive VIII + Dispersant | 150 + 150 | <3.0 | 44 |
| Additive VIII + Dispersant | 200 + 200 | 2.5 | 51 |
| Additive VIII + Dispersant | 66.7 + 33.3 | 3.5 | 31 |
| Additive VIII + Dispersant | 200 + 100 | 3.0 | 41 |

| Test Method: 12 weeks storage at 110 degrees F. | | | |
| --- | --- | --- | --- |
| Additive | Conc(lb/mbbl) | D-1500 Color | % T | Insoluble Residue mg/100 mL |
| Blank | — | 4.0 | 14 | 2.1 |
| Additive VIII + Dispersant | 50 + 50 | <4.0 | 21 | 1.4 |
| Additive VIII + Dispersant | 100 + 100 | 3.5 | 24 | 2.0 |
| Additive VIII + Dispersant | 150 + 150 | <3.5 | 27 | 1.8 |
| Additive VIII + Dispersant | 200 + 200 | <3.5 | 33 | 1.5 |
| Additive VIII + Dispersant | 66.7 + 33.3 | <4.0 | 19 | — |
| Additive VIII + Dispersant | 200 + 100 | 3.5 | 25 | 1.9 |

EXAMPLE 8

The 2:1 molar condensate of cyclohexanone and 1-piperazineethanamine (Additive VIII) was tested as a sweetener, i.e., in the context of distillate fuels a scavenger for mercaptans, under the following conditions:

When 1400 ppm of Additive VIII was added to a straight run kerosene to which 1422.5 ppm S had been added as hydrogen sulfide, 679.8 ppm of hydrogen sulfide remained.

When 70 ppm of Additive VIII was added to a diesel fuel containing 4.7 ppm S measured as hydrogen sulfide, the amount of S was reduced to 0.

When 140 ppm and 210 ppm of Additive VIII was added to a diesel fuel to which 805.5 ppm thiophenol had been added, the remaining S measured as hydrogen sulfide was reduced to 756.9 ppm and 716.6 ppm, respectively.

In view of the above, it will be seen that the several objects of the invention are achieved and other advantageous results attained. As various changes could be made in the above described methods and products without departing from the scope of the invention it is intended that all matter contained in the above description shall be interpreted as illustrative and not in a limiting sense.

What is claimed is:

1. A distillate fuel oil containing a stabilizing amount of an imine-enamine additive which is the condensation product of a member selected from the group consisting of aldehydes having at least two carbon atoms, ketones and mixtures thereof of the formula

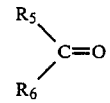

wherein $R_5$ is a member selected from the group consisting of alkyl, aryl, aralkyl alkaryl, cycloalkyl and heterocyclyl and $R_6$ is a member selected from the group consisting of hydrogen, alkyl, aryl, aralkyl, alkaryl, cycloalkyl and heterocyclyl, and a polyamino compound of the formula

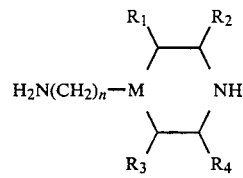

where n is 0 or an integer from 1 to 6, M is CH or nitrogen and $R_1$, $R_2$, $R_3$ and $R_4$ are independently selected from the group consisting of hydrogen, alkyl, aryl, aralkyl, alkaryl, cycloalkyl, alkenyl, aralkenyl, alkenylaryl, cycloalkenyl and heterocyclyl groups.

2. The distillate fuel oil of claim 1 wherein the polyamino compound is a mixture of said polyamino compounds.

3. The distillate fuel oil of claim 1 wherein the condensation product is produced from a reaction mixture in which the member selected from the group consisting of aldehydes, ketones and mixtures thereof and the polyamino compound are in a molar ratio from about 1:1 to about 2:1.

4. The distillate fuel oil of claim 3 wherein the fuel oil is a No. 1, 2 or 3 fuel oil from a naphthenic crude and wherein the additive is added in an amount effective to improve the color stability of said fuel oil.

5. The distillate fuel oil of claim 3 wherein the fuel oil is a No. 4 or 6 fuel oil from a naphthenic crude and wherein the additive is added in an amount effective to sweeten, retard sedimentation or sweeten and retard sedimentation thereof.

6. The distillate fuel oil of claim 3 wherein the ketone is cyclohexanone and the polyamino compound is 1-piperazineethanamine 7. A method for stabilizing a distillate fuel oil which comprises incorporating therein an effective amount of an imine-enamine additive which is the condensation product of a member selected from the group consisting of aldehydes having at least two carbon atoms, ketones and mixtures thereof of the formula

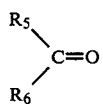

wherein $R_5$ is a member selected from the group consisting of alkyl, aryl, aralkyl, alkaryl, cycloalkyl and heterocyclyl and $R_5$ is a member selected from the group consisting of hydrogen, alkyl, aryl, aralkyl, cycloalkyl, and heterocyclyl, and a polyamino compound of the formula

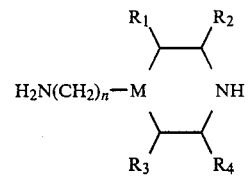

wherein n is 0 or an integer from 1 to 6, M is CH or nitrogen and $R_1$, $R_2$, $R_3$ and $R_4$ are independently selected from the group consisting of hydrogen, alkyl, aryl aralkyl, alkaryl, cycloalkyl, alkenyl, aralkenyl, alkenylaryl, cycloalkenyl and heterocyclyl groups.

8. The method of claim 7 wherein the polyamino compound is a mixture of said polyamino compounds.

9. The method of claim 7 wherein the condensation product is produced from a mixture in which the member selected from the group consisting of aldehydes, ketones and mixtures thereof and the polyamino compound are in a molar ratio from about 1:1 to about 2:1.

10. The method of claim 9 wherein the fuel oil is a No. 1, 2 or 3 fuel oil from a naphthenic crude and wherein the additive is added in an amount effective to improve the color stability of said fuel oil.

11. The method of claim 9 wherein the fuel oil is a No. 4 or 6 fuel oil from a naphthenic crude and wherein the additive is added in an amount effective to sweeten, retard sedimentation or sweeten and retard sedimentation thereof.

12. The method of claim 9 wherein the ketone is cyclohexanone and the polyamino compound is 1-piperazineethanamine.

* * * * *